(12) United States Patent
Sussman et al.

(10) Patent No.: US 10,314,548 B2
(45) Date of Patent: Jun. 11, 2019

(54) METHOD FOR T1 MAPPING WITH INCOMPLETE TISSUE MAGNETIZATION RECOVERY

(71) Applicant: UNIVERSITY HEALTH NETWORK, Toronto (CA)

(72) Inventors: Marshall Stephen Sussman, Toronto (CA); Bernd Juergen Wintersperger, Toronto (CA); Kai-Ho Fok, Mississauga (CA); Issac Yiqun Yang, Toronto (CA)

(73) Assignee: University Health Network, Toronto (CA)

( * ) Notice: Subject to any disclaimer, the term of this patent is extended or adjusted under 35 U.S.C. 154(b) by 124 days.

(21) Appl. No.: 15/514,323

(22) PCT Filed: Sep. 24, 2015

(86) PCT No.: PCT/CA2015/050951
§ 371 (c)(1),
(2) Date: Mar. 24, 2017

(87) PCT Pub. No.: WO2016/044943
PCT Pub. Date: Mar. 31, 2016

(65) Prior Publication Data
US 2017/0245807 A1 Aug. 31, 2017

Related U.S. Application Data

(60) Provisional application No. 62/055,708, filed on Sep. 26, 2014, provisional application No. 62/085,701, filed on Dec. 1, 2014.

(51) Int. Cl.
*G01R 33/50* (2006.01)
*G01R 33/54* (2006.01)
(Continued)

(52) U.S. Cl.
CPC .......... *A61B 5/7278* (2013.01); *A61B 5/0044* (2013.01); *A61B 5/055* (2013.01);
(Continued)

(58) Field of Classification Search
CPC .. G01R 33/50; G01R 33/543; G01R 33/5614; A61B 2576/023; A61B 5/7278; A61B 5/0044; A61B 5/7207
See application file for complete search history.

(56) References Cited

U.S. PATENT DOCUMENTS

2013/0154638 A1   6/2013   Jena et al.

FOREIGN PATENT DOCUMENTS

WO   2013140356 A1   9/2013

OTHER PUBLICATIONS

Canadian Intellectual Property Office, "International Search Report and Written Opinion" for corresponding International Application No. PCT/CA2015/050951 dated Dec. 11, 2014.
(Continued)

*Primary Examiner* — Rodney A Bonnette
(74) *Attorney, Agent, or Firm* — Ridout & Maybee LLP

(57) ABSTRACT

Methods and systems for performing T1 mapping. T1 samples are obtained from an acquisition including one or more inversion groupings. The acquisition may be designed to result in incomplete tissue magnetization recovery between inversion groupings. The acquisition may be designed for the use of non-uniform, non-180° preparatory pulses. The method may also include the combined use of data from different inversion groupings. A model is used in which fit parameters are variable dependent on the inversion grouping.

20 Claims, 12 Drawing Sheets

(51) Int. Cl.
 A61B 5/00 (2006.01)
 A61B 5/055 (2006.01)
 G01R 33/561 (2006.01)
(52) U.S. Cl.
 CPC .......... *G01R 33/50* (2013.01); *G01R 33/543* (2013.01); *A61B 5/7207* (2013.01); *A61B 2576/023* (2013.01); *G01R 33/5614* (2013.01)

(56) References Cited

OTHER PUBLICATIONS

European Patent Office, "European Search Report" for corresponding European Patent Application No. 15844590.8 dated Jun. 15, 2018.
Nekolla S., et al., "T1 Maps by K-Space-Reduced Snapshot-Flash MRI", Journal of Computer Assisted Tomogr, New York, NY, US., vol. 16, No. 2, Mar. 1, 1992, pp. 327-332.
Messroghli et al., "Optimization and validation of a fully-integrated pulse sequence for modified look-locker inversion-recovery (MOLLI) T1 mapping of the heart", Journal of Magnetic Resonance Imaging , vol. 25, No. 4, Sep. 25, 2007, pp. 1081-1086.
Weingartner et al., "Free-breathing multislice native myocardial T1 mapping using the slice-interleaved T1 (STONE) sequence", Magnetic Resonance in Medicine, vol. 74, No. 1, Aug. 1, 2014, pp. 115-124.
Kellman et al., "Adiabatic inversion pulses for myocardial T1 mapping", Magnetic Resonance in Medicine, vol. 71, No. 4, May 30, 2013, pp. 1428-1434.
Piechnik et al., "Shortened Modified Look-Locker Inversion Recovery (ShMOLLI) for clinical myocardial T1-mapping at 1.5 and 3T within a 9 heartbeat breathhold", Journal of Cardiovascular Magnetic Resonance, Biomed Central Ltd, London UK, vol. 12, No. 1, Nov. 19, 2010, p. 69.
Messroghli et al., "Modified Look-Locker inversion recovery (MOLLI) for high-resolution T1 mapping of the heart", Magnetic Resonance in Medicine, vol. 52, No. 1, Jun. 28, 2004, pp. 141-146.

METHOD FOR T1 MAPPING WITH INCOMPLETE TISSUE MAGNETIZATION RECOVERY

CROSS-REFERENCE TO RELATED APPLICATIONS

The present disclosure claims priority from U.S. provisional patent applications Nos. 62/055,708 and 62/085,701, the entireties of which are hereby incorporated by reference.

FIELD

The present disclosure relates to magnetic resonance imaging (MRI) techniques. In particular, the present disclosure relates to techniques for cardiac MRI.

BACKGROUND

At the very beginning of a typical magnetic resonance (MR) scan, magnetization is lined up in the direction of the main magnetic field. When the MR scan begins, one or more radiofrequency (RF) pulses may be applied to the magnetization. These pulses tip the magnetization away from the direction of the main magnetic field. If no more RF pulses occur, the magnetization begins to recover back toward is initial value. The rate at which the magnetization recovers is referred to as its "$T_1$ value". $T_1$ is a characteristic property of tissue. It may be altered in the presence of pathology.

In conventional MRI, scans are typically performed that emphasize the differences in $T_1$ between tissues and pathology. This is typically accomplished as follows: an initial RF pulse is applied; following this pulse, a delay period then occurs; during this period, the magnetization recovers back toward its equilibrium value. However, different tissues and pathology will in general have difference $T_1$ values. Therefore, after the delay period, magnetization from different tissues/pathology will in general have recovered to different levels. In conventional MRI, a single image is typically acquired after the delay period. This produces an image that is referred to as a "$T_1$-weighted" image, which may provide $T_1$ information in a qualitative manner. In a $T_1$-mapping scan, multiple images at different delay times are acquired. At each delay period, the magnetization will have recovered to a different level. In this manner, one can follow the magnetization as it recovers to its equilibrium value. To determine a tissue's $T_1$ value, a mathematical model is fit to this recovery curve. One of the parameters of the model is the tissue $T_1$ value. Note that this fitting procedure is performed on every pixel in the image. Therefore, the $T_1$ value in each pixel may be determined. If these $T_1$ value are displayed in an image format, the resulting image is referred to as a "$T_1$ map", which may provide $T_1$ information in a quantitative manner.

Quantitative $T_1$ mapping has shown promise for early identification and discrimination of pathology in a wide range of cardiac diseases. The success of these techniques may be dependent on an accurate, precise, and clinically practical cardiac $T_1$ mapping technique. One $T_1$ mapping technique in particular, Modified Look-Locker Inversion Recovery (MOLLI), has attracted much recent attention [1,2]. A typical MOLLI acquisition is illustrated in FIG. 1.

The basic MOLLI sequence of FIG. 1 begins with a 180° inversion pulse triggered by the R-wave of the cardiac cycle. A steady-state free precession (SSFP) readout is then performed to acquire the first inversion time ($TI_1$). The SSFP readout may then be acquired on subsequent cardiac cycles to acquire additional inversion times ($TI_2$). This forms the first inversion grouping. Typically, a maximum of five inversion times may be acquired before the magnetization reaches its steady state. In theory, a $T_1$ map could be calculated from these inversion times alone [3]. However, in the interest of improving the precision of the fit, additional data is typically acquired. Therefore, the entire process, beginning with another inversion pulse, is repeated to collect $TI_3$, $TI_4$, $TI_5$. If appropriate, this process may be repeated as necessary to acquire additional inversion groupings. This forms the second inversion grouping. The separately-acquired data from all inversion groupings is subsequently combined. Curve fitting is then performed on the combined data set to calculate $T_1$. Note that in this particular example, two inversion times were acquired in the first group, and three in the second. However, this is just illustrated for example. In general, the distribution of inversion times within each inversion group may be selected to be any suitable combination.

However, the data combination presents a problem: unless the magnetization fully recovers to its equilibrium value at the end of each inversion grouping, the initial magnetization in subsequent inversion groupings will in general be different. In turn, this will lead to discontinuities in the combined data, and consequently errors in the $T_1$ curve fit. To address this issue, conventional MOLLI techniques use an additional "rest period" during which the magnetization is allowed to recover back to its equilibrium value. (In the present disclosure, the acquisitions will be labeled as "w(x)y", where the non-bracketed numbers indicate an inversion grouping, and the bracketed numbers indicate a rest period, indicated as a count of heartbeats.) Unfortunately, these rest periods can significantly reduce the efficiency and/or lengthen the scan time—a three heartbeat rest period is typical. Furthermore, if the rest period is not long enough, systematic errors in the curve fit may result. This may be a particular problem in patients with faster heart rates. There may be additional limitations or disadvantages in the conventional approach. For example, if an arrhythmia occurs during the rest period, this could artificially shorten the recovery period (since the rest period is based on the number of heartbeats), and thus may lead to incomplete magnetization recovery. Further, if a free-breathing navigator scan is desired, the added time required for the rest period may make the scans impractically long. Using a fixed-rate rest period, rather than one based on heart beats may reduce or minimize some of the issues associated with heart-rate sensitivity. However, such an approach may still incur a significant efficiency penalty.

Another issue associated with conventional MOLLI is that the calculated T1 value may exhibit a bias relative to the true T1 value. In conventional MOLLI, this is typically partially (but not completely) removed with a correction factor [1]. The effectiveness of this correction factor may be compromised in the absence of complete magnetization recovery between inversion groupings.

An attempt at reducing the requirement for the MOLLI rest period is the ShMOLLI technique [3,4]. Like conventional MOLLI, ShMOLLI still requires full magnetization recovery for fitting. To ensure this occurs, a conditional fitting algorithm is employed which selectively removes inversion times that did not start from the full equilibrium magnetization. There are a number of disadvantages with this approach: first, for tissues with longer $T_1$s, there are potentially only a limited number of data points available for fitting—typically a single inversion grouping with a maximum of ~5 points. This limits the precision of the fits. The variable number of fitted points could also lead to added variability in the precision of the fits across tissue types/pathology with different $T_1$ values. Second, ShMOLLI typically does not eliminate the rest period, but rather reduces it to one heart beat. Third, typical ShMOLLI implementations to date have used exactly the same inversion grouping for data acquisition. While it may be possible to employ a ShMOLLI approach with other inversion groupings, the algorithm would likely have to be re-tuned and possibly re-validated for each specific case.

SUMMARY

In various examples, the present disclosure describes a technique to enable generation of $T_1$ maps even in the presence of incomplete tissue magnetization recovery, which technique may serve as an alternative to the conventional MOLLI technique. Examiner of this technique is referred to herein as Inversion Group (IG) fitting. Using examples of IG fitting disclosed herein, accurate $T_1$ maps may be achieved for any arbitrary combination of inversion groupings and rest periods (including no rest period). The flexibility of this technique may be used to shorten the acquisition period whilst maintaining $T_1$ accuracy, to acquire more TI's in the equivalent scan time as a conventional MOLLI approach, or more generally to allow greater flexibility in selecting TI's and flip angles for the purpose of optimization (of accuracy, precision, etc.). It may also provide more robustness over a range of different heart rates. In some examples, the disclosed approach may address one or more of the above-discussed drawbacks of conventional techniques. An example application that may benefit from the present disclosure is acquisitions that use motion compensation. Additionally, this same approach could also be applied to grouped fitting scenarios other than a $T_1$ MOLLI acquisition, as well as to other area besides the heart.

In some examples, the present disclosure provides a method for determining T1 value, which may include: obtaining T1 samples from an acquisition that includes at least two inversion groupings; applying a model in which fit parameters are variable dependent on each inversion grouping; and determining a true T1 value using the fit parameters calculated using the model. In some examples, the present disclosure further provides a method for generating a $T_1$ map, using an example of the above-described method. Although the present disclosure describes examples in which the disclosed technique is used with acquisitions including at least two inversion groupings, it should be understood that the present disclosure may similarly apply to acquisitions having only one inversion grouping.

In some examples, the present disclosure also provides systems and computer readable media for determining T1 value.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

A technique for $T_1$ fitting of MOLLI data is disclosed herein. In the disclosed examples, two parameters are used, plus one additional parameter per inversion grouping. The present disclosure may be useful in that it may permit the use of any combination of inversion groupings and rest periods (including no rest period), including acquisitions in which there is incomplete tissue magnetization recovery between inversion groupings. In various examples, the present disclosure may enable the generation of $T_1$ maps in the presence of incomplete tissue magnetization recovery between inversion groupings, as well as in other acquisitions where there incomplete magnetization recovery is not present or is not a concern. It may also permit the use of preparatory pulses with a range of flip angles, rather than being limited to a 180° flip angle uniform across all inversion groupings.

In the conventional MOLLI fitting algorithm [1], signal behavior of all inversion groupings may be modeled by the three parameter SNAPSHOT-FLASH equation [5]:

$$S(TI) = A - Be^{-\frac{TI}{T_1^*}} \quad (1)$$

where $T_1^*$ is the "apparent" or observed longitudinal relaxation rate, related to the true relaxation rate ($T_1$) by:

$$T_1 = T_1^* \cdot \left(\frac{B}{A} - 1\right) \quad (2)$$

Figure 1:
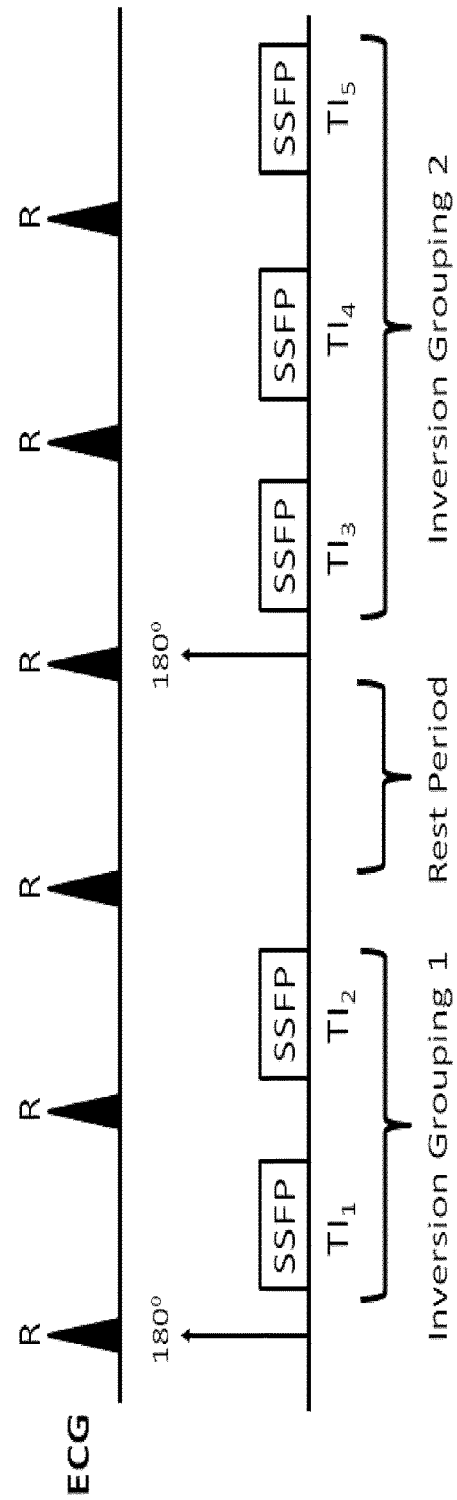
FIG. 1 shows an example of the basic MOLLI sequence.
Figure 2:
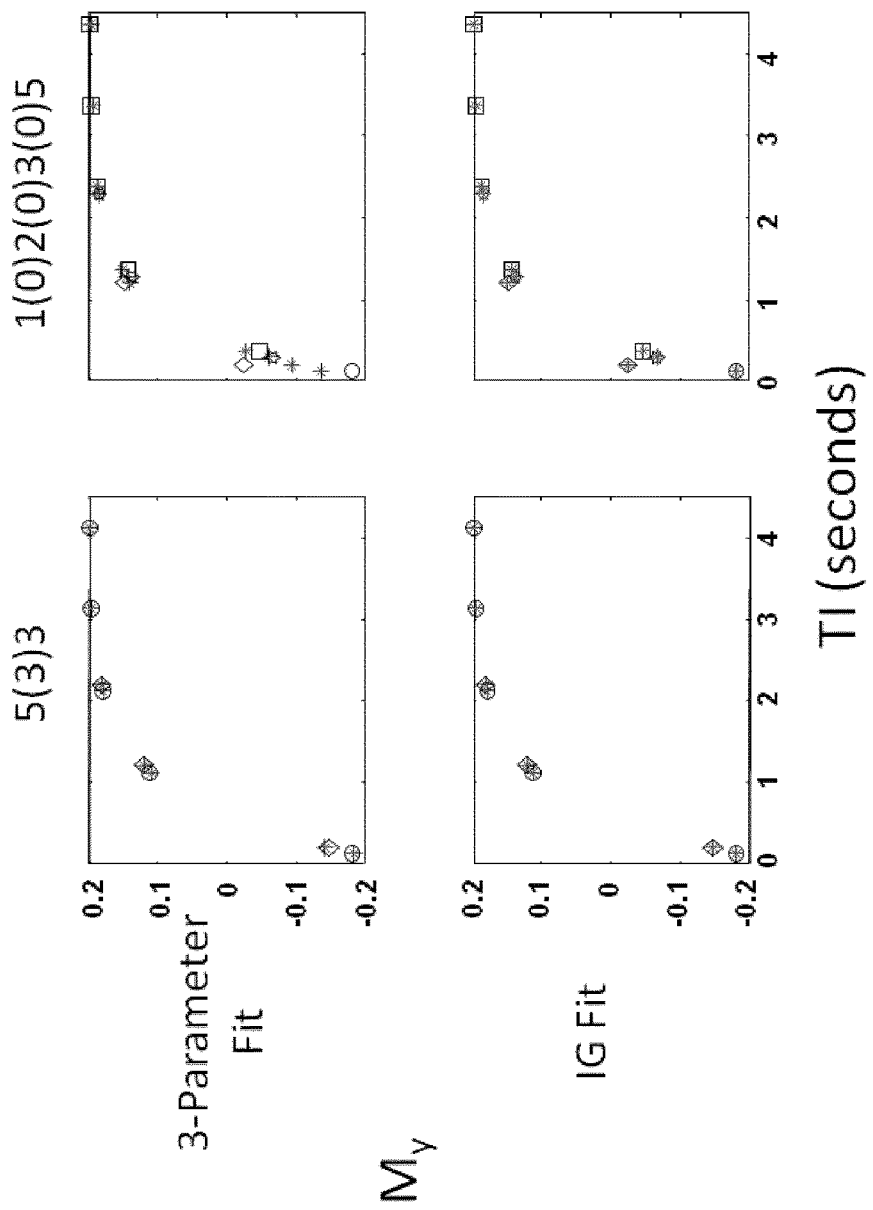
FIG. 2 shows plots of simulated T1 fits comparing the MOLLI technique with an example of the present disclosure.

Provided all inversion groupings start from the same initial magnetization, Eq. 1 is valid. In conventional MOLLI, such a condition is achieved with the use of long rest periods to allow full recovery back to equilibrium prior to the next inversion pulse. If the rest period is shortened (or eliminated), then the magnetization of all inversion groupings cannot be described by a single equation. An example of this is illustrated in FIG. 2, described further below.

In examples of the IG fitting technique, it is assumed that signal behavior is governed by the SNAPSHOT-FLASH equation. However, unlike conventional MOLLI, there is no assumption that the magnetization recovers back to equilibrium (or even to the same non-equilibrium value) on each inversion grouping. To account for this increased freedom, the possibility that the parameters of the equations may be different for each of the n inversion groupings is taken into account:

$$S_i(TI) = A_i - B_i e^{-\frac{TI}{T_{1_i}^*}}; i = 1, \ldots, n \quad (3)$$

$A_i$ and $B_i$ can be expressed explicitly in terms of the steady state magnetization for each inversion grouping ($M0_i^*$), the magnitude of the magnetization immediately prior to each 180° inversion pulse ($M0_i$), the equilibrium magnetization (M0), $T_1^*$, and $T_1$[5,6]:

$$A_i = M0_i^* \quad (4)$$

$$B_i = (M0_i + M0_i^*) \quad (5)$$

$$M0_i^* = M0\left(\frac{T_{1_i}^*}{T_1}\right) \quad (6)$$

At this stage, there are three parameters ($A_i, B_i, T_{1_i}^*$) for each inversion grouping. However, it is possible to significantly reduce this number: First, as shown below, the steady state magnetization for any inversion grouping (with the same SSFP readout, flip angles, etc.) is always the same:

$$A_1 = A_2 = \ldots = A_n \equiv A \quad (7)$$

Figure 3:
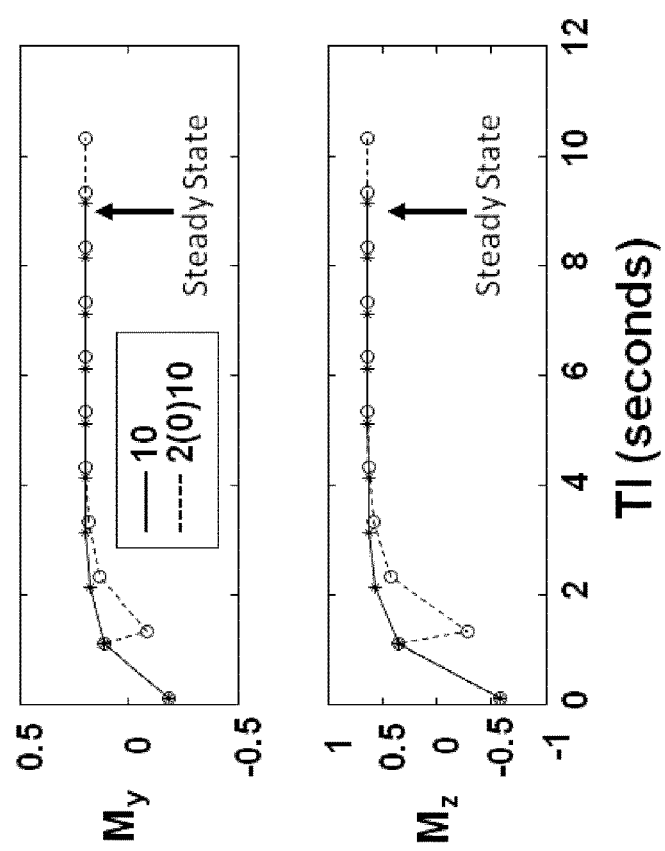
FIG. 3 shows plots illustrating the steady state independent of the MOLLI technique.

To illustrate this point, FIG. 3 shows an example of two different inversion groupings with the same steady state. In FIG. 3, two different inversion groupings are simulated. The first simply acquires 10 inversion times. The second acquires an initial inversion grouping of two inversion times, followed by a second grouping of 10 inversion times. In both cases, the steady state magnetization is the same. Note that both simulations used the same acquisition parameters (flip angle, number of phase encode lines, etc.).

The following discussion shows that, for a given set of pulse sequence parameters (flip angle, matrix size, etc.), the steady state of any MOLLI inversion grouping is the same (i.e. Eq. 7). Since all pulse sequence parameters are selected to be the same, the only difference between inversion groupings is therefore the starting point of the magnetization. Therefore, to satisfy Eq. 7, the MOLLI steady state should be independent of the initial magnetization at the beginning of any inversion grouping.

Figure 7:
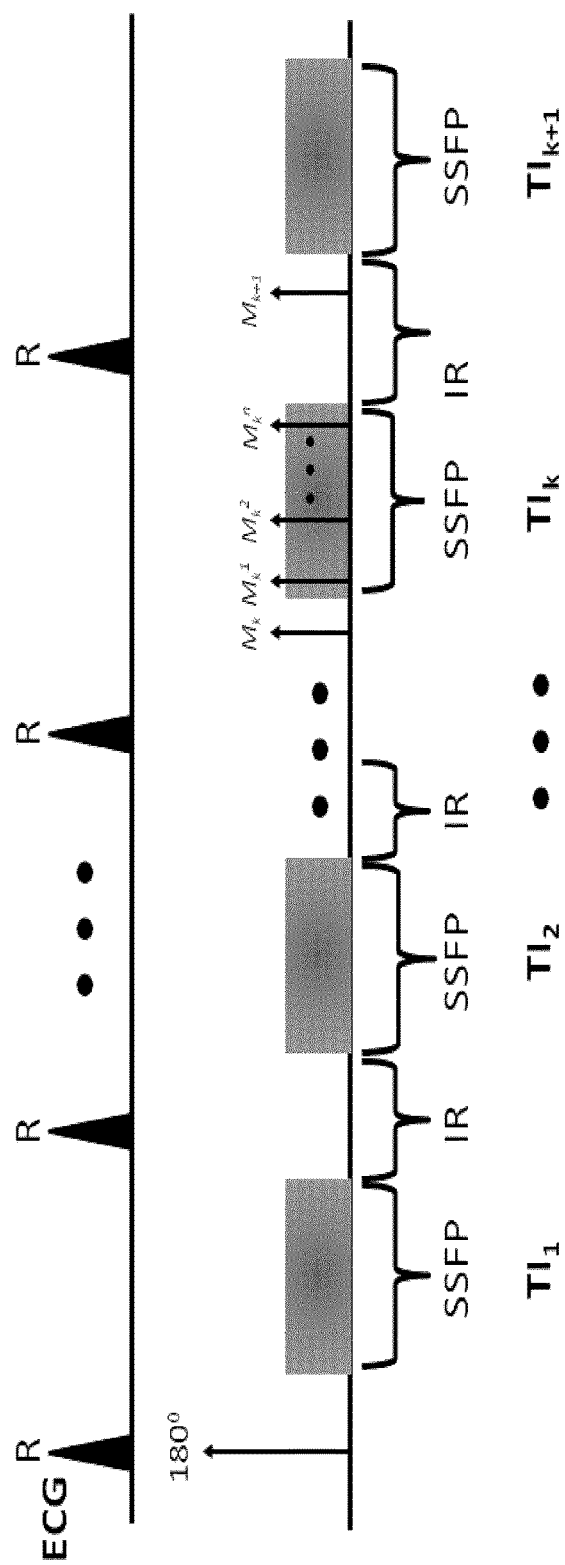
FIG. 7 is a schematic of a MOLLI acquisition.

An expression for the steady state magnetization can be derived. Reference to FIG. 7 may help in understanding the following discussion. FIG. 7 is a schematic of an example MOLLI acquisition. The pulse sequence begins with a 180° pulse. The basic MOLLI acquisition unit then consists of an SSFP acquisition (shaded box) followed by an inversion recovery period (IR). Each TI used in the subsequent fit is acquired during the SSFP period. The magnetization immediately preceding the $k^{th}$ SSFP acquisition is labeled $M_k$. During the subsequent SSFP acquisition, the magnetization is labeled as $M_k^i$, where i indicates the $i^{th}$ SSFP period. In the steady state, $M_k = M_k + 1$.

It may be assumed (to be proven later) that the magnetization just prior to the SSFP acquisition of the $k^{th}$ inversion grouping is related to the $k+1^{th}$ point (see FIG. 7) through a linear matrix equation:

$$M_{k+1} = AM_k + B \quad [A1]$$

In the steady state, by definition: $M_{k+1} = M_k \equiv M_{SS}$. Therefore:

$$M_{SS} = (I-A)^{-1}B \quad [A2]$$

where I is the identity matrix.

To prove that the steady state is independent of the initial magnetization, it must be proven that:

1) The MOLLI pulse sequence can be described by Eq. A1
2) A and B are not functions of the initial magnetization.

To prove points #1 and #2, the matrix description of magnetization can be utilized [7,8].

The MOLLI pulse sequence has an SSFP acquisition followed by a period of free inversion recovery. The SSFP component can first be characterized. Note that unlike a conventional SSFP acquisition, MOLLI acquisitions do not achieve the SSFP steady state (otherwise, the magnetization would be the same for all TI's, since the SSFP steady state is independent of the initial magnetization [7]). Therefore the transient SSFP response should be analyzed. The magnetization immediately prior to the $k^{th}$ SSFP readout in an inversion grouping may be defined as $M_k$ (see FIG. 7). Next, the magnetization at the $i^{th}$ period of the subsequent SSFP readout may be defined as $M_k^{i+1}$. The magnetization during the first (i.e. i=1) SSFP period is given by:

$$M_k^1 = FM_k + G \quad [A3]$$

F and G are products of rotation and relaxation matrices, as shown in Ref. [7]. The magnetization at the second SSFP period will be given by:

$$M_k^2 = FM_k^1 + G \quad [A4]$$

$$= F^2 M_k + FG + G \quad [A5]$$

Continuing this process, it can be shown that the magnetization after the $n^{th}$ and final SSFP period will be given by:

$$M_k^n = F^n M_k + \left(\sum_{i=0}^{n-1} F^i\right) G \quad [A6]$$

$$= F^n M_k + (I-F)^{-1}(I-F^n) \cdot G \quad [A7]$$

where Eq. A7 is derived from Eq. A6 by employing the formula for a matrix geometric sum.

Equation A7 represents the magnetization at the end of the SSFP readout. The subsequent free inversion recovery period can also be described in a similar matrix format:

$$M_{k+1} = F'M_k^n + G' \quad [A8]$$

where F' and G' are again combinations of rotations (for off-resonance magnetization) and relaxation matrices. The "prime" superscript is meant to indicate that the parameters of these matrices will be different than those in Eq. A3.

Inserting Eq. A7 into A8, the validity of Eq. A1 (and point #1) may be confirmed for the MOLLI sequence if it is defined:

$$A = F'F^n \quad [A9]$$

$$B = F'(I-F)^{-1}(I-F^n)G + G' \quad [A10]$$

Finally, to verify point #2, it may be noted that all matrices describing the steady state magnetization (i.e. F,G, F', G') consist purely of rotations and relaxations. In particular, they do not depend on the starting conditions of the magnetization. This, it can be proved that the steady state of any MOLLI inversion grouping is the same.

Using Eqs. 4, 6 and 7, it is straightforward to show that:

$$T_{1_i}^* = T_{1_2}^* = \ldots = T_{1_n}^* = T_1^* \quad (8)$$

With Eqs. 7 and 8, the number of free parameter is reduced to two plus the number of inversion groupings. A simplified equation describing the signal behavior of all inversion groupings can then be derived from Eq. 3 as:

$$S_i(A, B_1, \ldots, B_i, T_1^*; TI) \equiv A - B_i e^{-\frac{TI}{T_1^*}}; i = 1, \ldots, n \quad (9)$$

Another issue to be addressed is the extraction of the true $T_1$ value from the fitted parameters. Adapting the derivation performed in Kellman et al. [6] for use in the present case, the true $T_1$ value may be calculated from A, $T_1^*$, the $B_i$ parameter from the $i^{th}$ inversion grouping, and the fraction of magnetization ($\equiv \delta_i$) prior to the $i^{th}$ inversion pulse:

$$T_{1_i} = T_1^* \cdot \left(\frac{B_i}{A} - 1\right) / \delta_i \quad (10)$$

While it is possible to use Eq. 10 to derive $T_1$ from any inversion grouping, in practice, it may be simpler to use the first inversion grouping (i.e. i=1). In this case, $\delta_i$ is known to be always equal to one—the full equilibrium magnetization (unless $B_1$ inhomogeneities are present, which is dealt with in Ref. [6]). It should be noted that calculating $T_1$ from other inversion groupings may provide different $T_1$ precisions.

It may also be possible to derive $T_1$ from more than one inversion grouping. To do this, one needs to know or determine the $\delta_i$ of the inversion groupings being combined.

Various methods may be for determining $\delta_i$. In one example approach, the magnetization behavior may be simulated (with, for example, the Bloch Equations) to determine what inversion fraction is expected with the current acquisition and relaxation parameters.

Another example approach for determining $\delta_i$ is to calculate it from the MOLLI data itself. One possible approach is to calculate it from groups of pixels with similar uncorrected T1 values (i.e. without dividing by the inversion fraction). For each of the "i" inversion groups, a histogram may be formed consisting of "r" bins from its associated uncorrected T1 values. The mean value of each of the bins in the histogram may be calculated as follows:

$$T_{1_{hist_i}}^{uncorr} = \lfloor T_{1_1}^{uncorr}, T_{1_2}^{uncorr}, \ldots, T_{1_r}^{uncorr} \rfloor \quad (11)$$

A separate estimate of $\delta i$ may be formed for each of the bins in the histogram. This estimate may be defined as:

$$\delta_{i_r} = \frac{T_{1_r}^{uncorr}}{T_{1_1}^{uncorr}} \quad (12)$$

where the "i" subscript refers to the inversion group, and the "r" subscript refers to the bin number corresponding to that inversion group.

Figure 11:
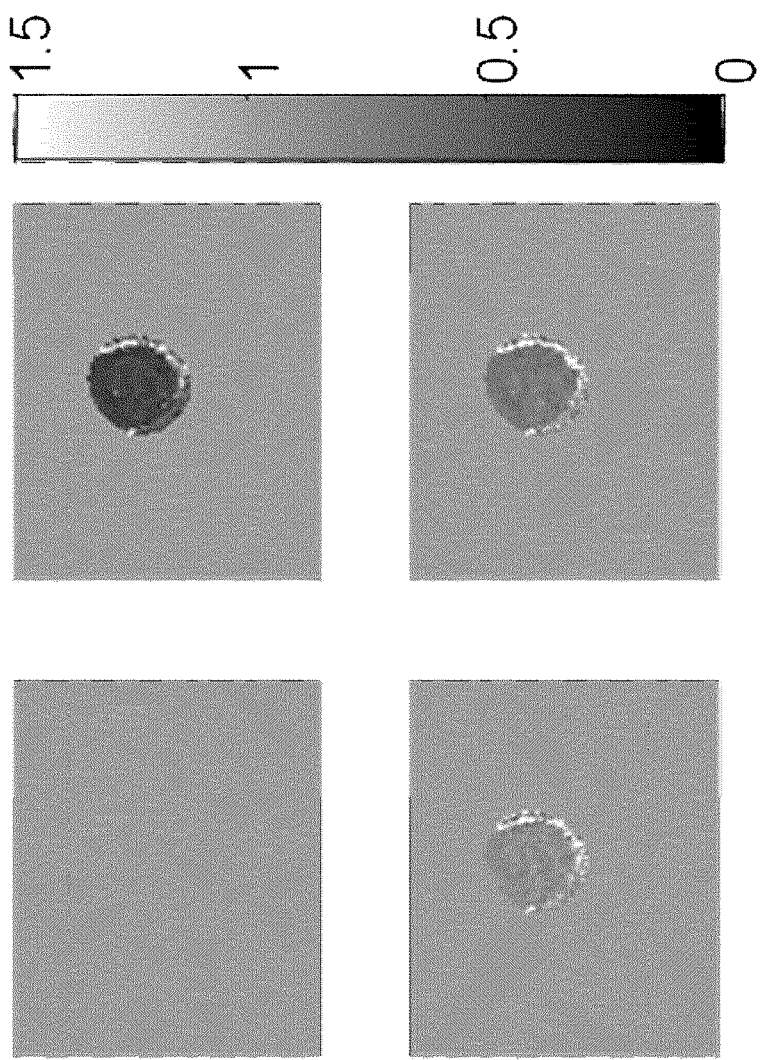
FIG. 11 illustrates an example of calculating a $\delta_i$ value in a MOLLI acquisition.
Figure 12:
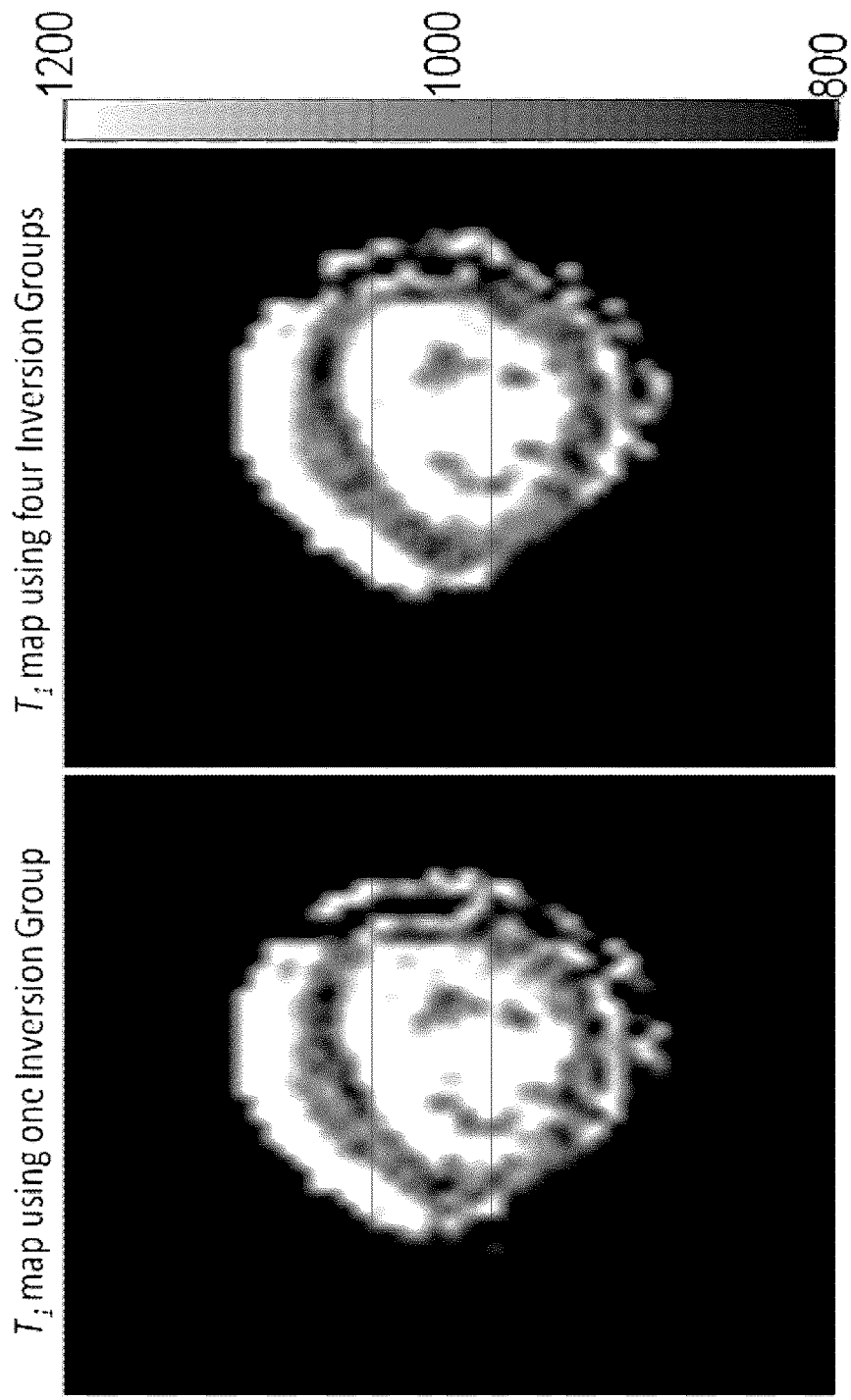
FIG. 12 shows example T1 maps calculated from the first inversion group only, and calculated from four inversion groups.

An example of this is illustrated in FIG. 11. In this case, $\delta i$ is calculated for each of the four inversion groups in a 1(0)2(0)3(0)5 MOLLI acquisition. To illustrate the utility of this information, the left hand side of FIG. 12 is the example T1 map calculated from the first inversion group only, while the right hand side is the example T1 map calculated from all four inversion groups. The resulting improvement in precision using all four inversion groups can be appreciated.

Another possible method for estimating the inversion fractions may be to calculate ratios of uncorrected T1 values over all pixels of the same tissue type.

With estimates of $T_1$ from all inversion groups, some or all of these values may be optionally combined together. This combination may, for example, improve the precision of the overall T1 estimate. There may be other possible methods of combination such as weighted mean, median, etc. One possibility, which may be useful from a precision perspective, is a sum of squares:

$$T_{1_{combined}} = \sqrt{\sum_{i=1}^{r} T_{1_i}^2} \quad (13)$$

Figure 10:
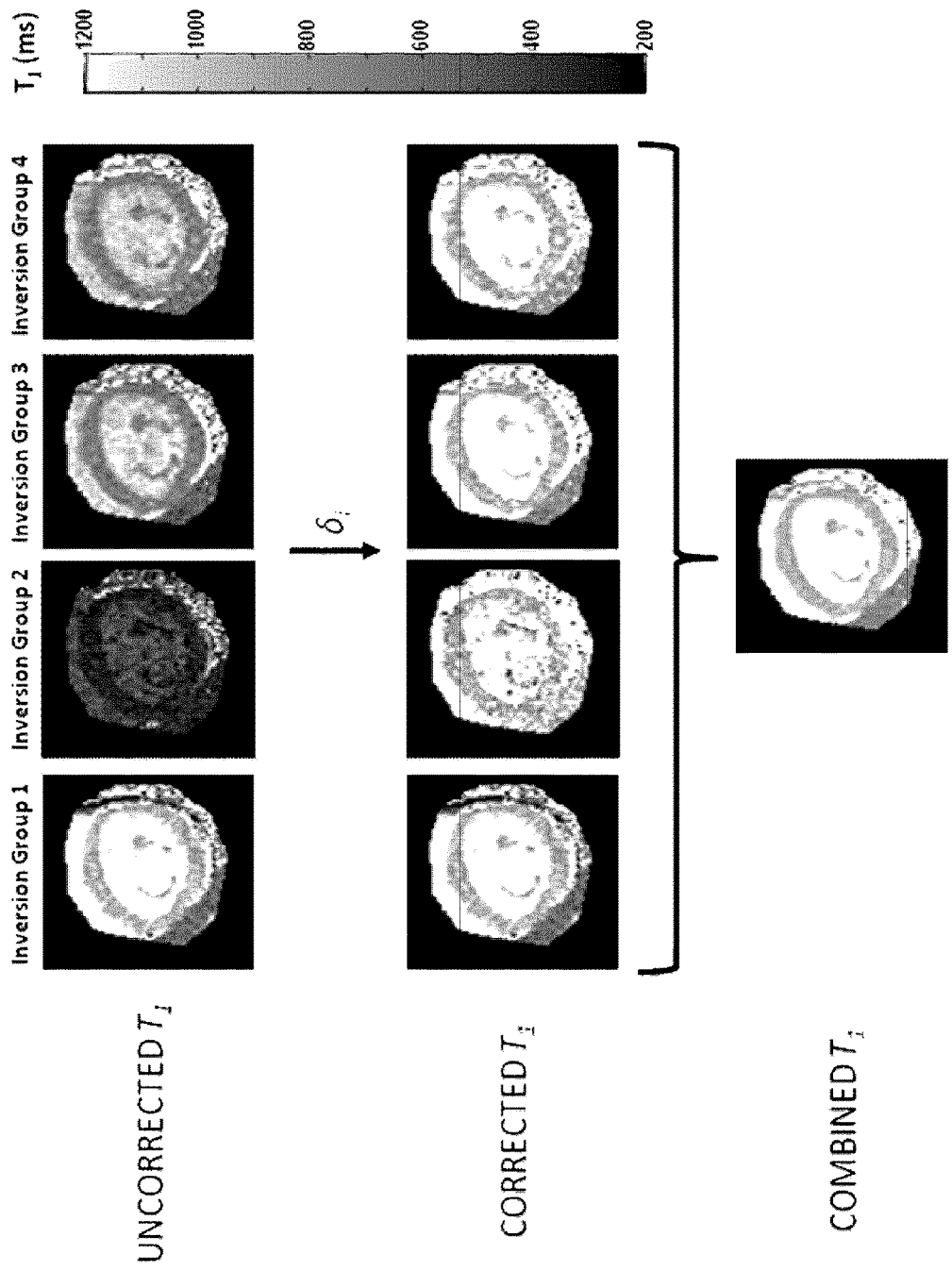
FIG. 10 shows an example T1 map generation achieved by combining T1 estimates from individual inversion groupings.

FIG. 10 illustrates an example of such an approach to combining T1 estimates. FIG. 10 shows the uncorrected $T_1$ maps from four inversion groups, which are corrected to generate four corrected $T_1$ maps. Finally, the four $T_1$ maps are combined (e.g., using a sum of squares approach) to generate a combined $T_1$ map.

Another possible advantage of examples of the disclosed technique is that it may permit the use of preparatory pulses other than 180° (as required in conventional MOLLI).

More generally, the preparatory pulses before each individual inversion grouping do not even have to be the same. This additional degree of freedom may be used to optimize various properties of the acquired data, such as accuracy and/or precision of T1 maps, for example.

It should also be noted that a similar technique could be applied to other fitting scenarios (besides $T_1$ mapping and MOLLI) that use groups of data separated by a rest period, as well as to other areas besides the heart.

Figure 8:
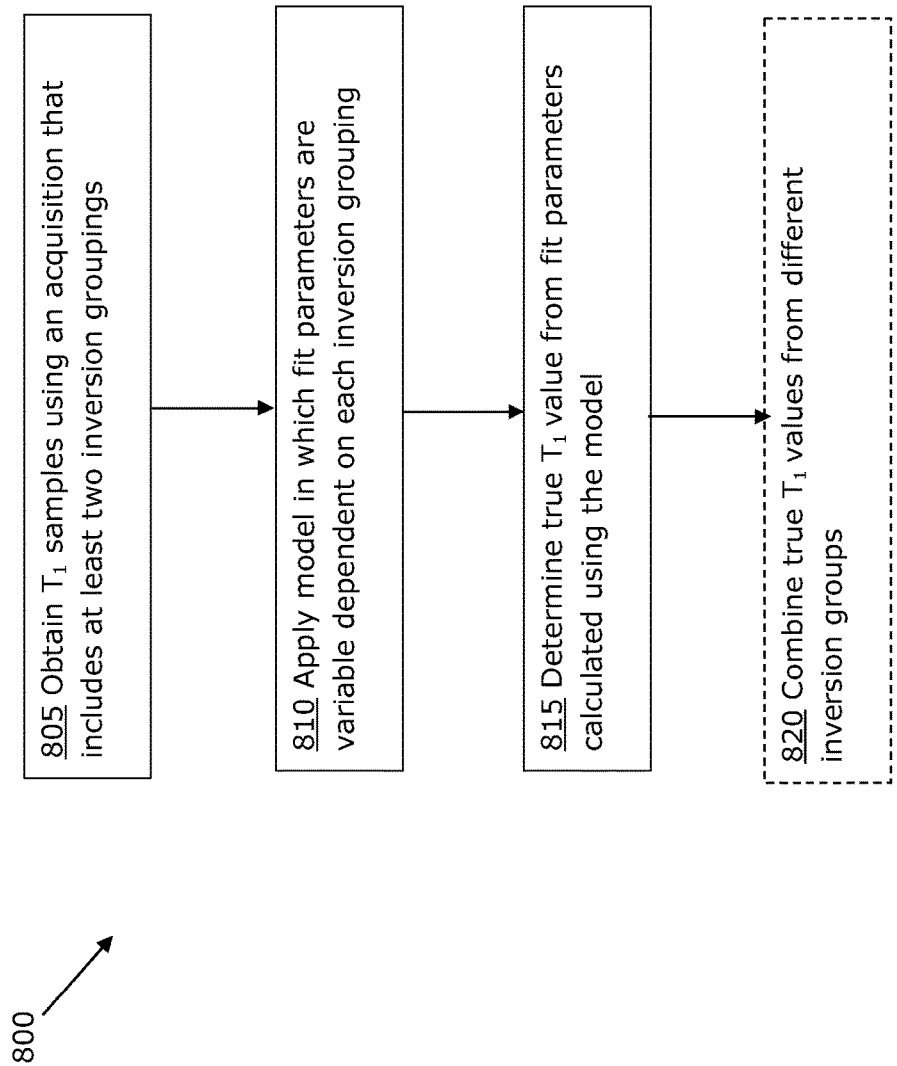
FIG. 8 is a flowchart of an example method for performing T1 fits.

FIG. 8 is a flowchart showing an example method 800 for performing an example of the disclosed IG fitting technique.

At 805, $T_1$ samples are obtained. This may involve performing and sampling from an acquisition that includes at least two inversion groupings, with or without a rest period between the groupings. The acquisition may be designed such that there is incomplete tissue magnetization recovery between inversion groupings. For example, there may be no rest period or only a short rest period (e.g., only one heartbeat in length). In other examples, the acquisition may allow for complete tissue magnetization recovery between inversion groupings, or there may be only one inversion grouping. In some examples, the $T_1$ samples may be obtained without performing the acquisition (e.g., previously sampled during a previous acquisition). For example, the method 800 may be retroactively applied to previously acquired $T_1$ samples (e.g., data retrieved from a historical database), and may be used to re-fit samples that were previously fitted according to conventional MOLLI techniques. In some examples, the preparatory pulses at the beginning of each inversion grouping may be uniformly 180°. In other examples, they may take on uniform values different than 180°. In other examples, they may take on non-uniform values that may or may not include 180°.

At 810, the model described above is applied to the samples. The model includes fit parameters (i.e., $B_i$) that are variable dependent on the inversion grouping. Suitable fitting techniques may be used to calculate or estimate the fit parameters. Using the model, the A, $T_1^*$ and $B_i$ values can be determined or estimated.

At 815, the true $T_1$ value may be determined from the fit parameters (i.e., A, $T_1^*$ and Bi) calculated from the model, using Eq. 10 above. This may be the case where the fitted $T_1$ value may not exactly equal the true $T_1$ value. Instead, it may have a bias. This may be a general property of all MOLLI-type acquisitions.

At 820, optionally, the true T1 values from one or more of the inversion groupings may be combined. For example, the inversion fractions of each inversion grouping may be calculated, and applied to each inversion group separately. In one example, the inversion fractions may be calculated from the Bloch Equations. In another example, they may be estimated from the images themselves. This may be accomplished by calculating the ratios of uncorrected T1 estimates of the different inversion groupings, for example. The corrected T1 estimates from one or more of the inversion groupings may then be combined together. In one example, they may be combined together in a weighted sum-of-squares manner.

The determined $T_1$ may be used to generate a $T_1$ map, using suitable techniques and software. The present disclosure may be useful in applications other than those specifically described herein. Some examples are described briefly below.

In most conventional implementations of MOLLI, the MR acquisitions were performed with the patient holding their breath for the duration of the scan. However, it is also possible to acquire a MOLLI-type of acquisition with the patient breathing freely. To minimize errors (or "artifacts") related to respiration, this type of scan typically requires some form of motion compensation—a typical example being the use of navigator echoes.

The drawback with most motion compensation schemes is that they typically require multiple reacquisitions of the data. These reacquisitions can result in a lengthy overall scan time. Therefore, a method that can reduce the overall scan time would provide a significant benefit in the case of a navigated scan. Since the disclosed IG fitting technique does not require rest periods, it could therefore provide time savings for a navigated MOLLI scan. This may also potentially facilitate the implementation of 3D-MOLLI acquisition.

In various examples described herein, the described techniques were discussed in the context of cardiac applications. However, examples of the present disclosure could also be extended to non-cardiac applications as well. For example, the present disclosure may be useful for situations in which the data from multiple $T_1$ recovery curves must be combined together. Such combinations may be desirable when the data from a single $T_1$ recovery curve does not provide sufficient precision. In the case of cardiac imaging, the data acquisitions typically are synchronized to the cardiac cycle. In non-cardiac applications, the data acquisitions may be instead separated by a specified interval of time. Other than this difference, the cardiac and non-cardiac IG techniques may be similar.

Various examples described herein have been described for the case of a MOLLI-type acquisition. However, the same or similar approach could also be applied to other related pulse sequences such as Look-Locker or SNAPSHOT-FLASH, among others. It may also be possible to adapt the same or similar approach to other types of acquisitions as well (e.g. inversion recovery).

Figure 9:
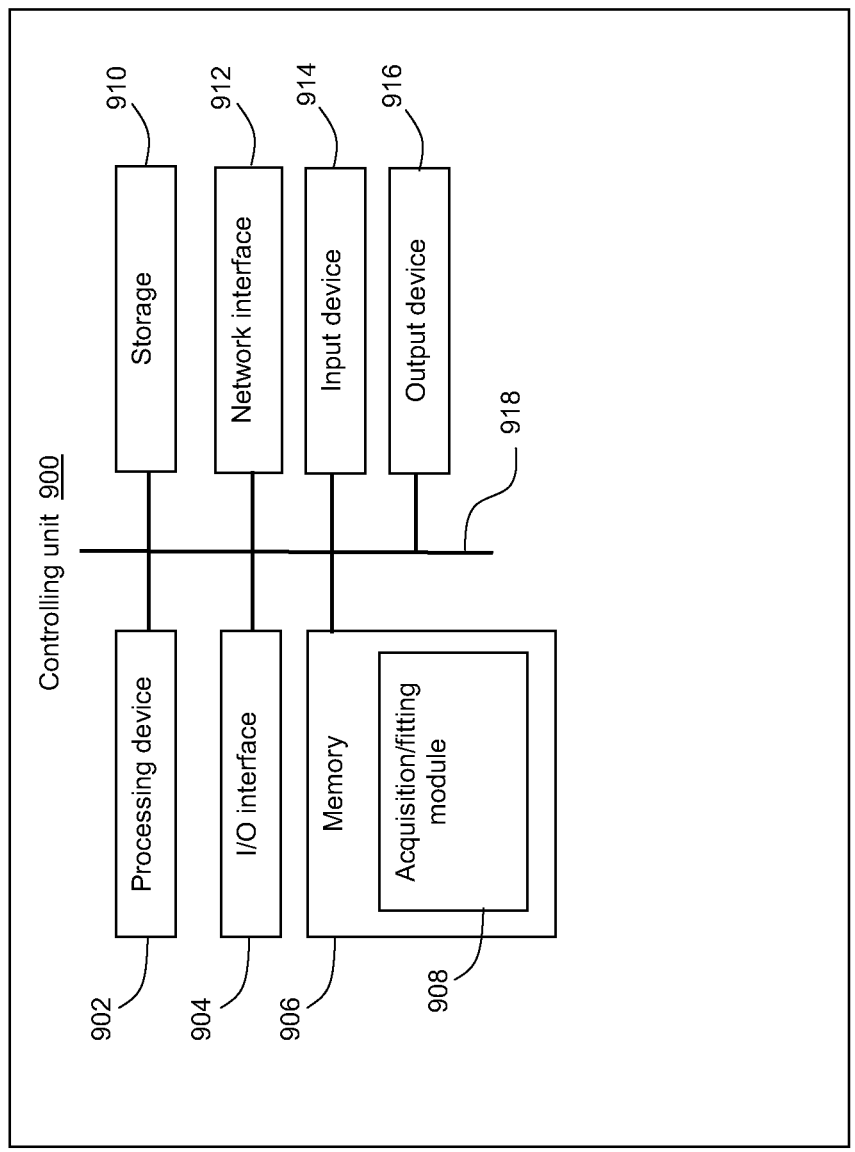
FIG. 9 is a schematic diagram of an example controlling unit suitable for carrying out an example of the present disclosure.

FIG. 9 is a schematic diagram of an example controlling unit 900, which may be used to implement an example of the disclosed IG fitting technique, such as the example method 800. The controlling unit 900 may be part of a MR workstation (e.g., a computer workstation operating MR-related software), or may be part of a MR scanner. The controlling unit 900 may be a desktop device or a portable device, for example.

The controlling unit 900 may include one or more processing devices 902, such as processor or a microprocessor. The controlling unit 900 may also include one or more input/output (I/O) interfaces 904, which may enable interfacing with one or more appropriate input and/or output devices, including one or more input devices 914 and/or one or more output devices 916 of the controlling unit 900. The controlling unit 900 may include one or more memories 906, which may include a volatile or non-volatile memory (e.g., RAM, ROM, hard drive, etc.).

The memory may have tangibly stored thereon an acquisition/fitting module 908, which includes instructions for carrying out aspects of the present disclosure, such as the example method 800 described above. For example, the acquisition/fitting module 908 may include software instructions for performing an example of the disclosed IG fitting technique. The acquisition/fitting module 908 may also include software instructions for carrying out the example acquisitions described herein (including acquisitions resulting in incomplete magnetization recovery between inversion groupings) for obtaining $T_1$ samples. In some examples, such as where the controlling unit 900 is part of a MR scanner or is part of a MR workstation that controls the MR scanner, the acquisition/fitting module 908 may include instructions that control operation of the MR scanner.

The memory(ies) 906 may include other software instructions, such as an operating system and other applications. In some examples, the acquisition/fitting module 908 may be provided by an external memory (e.g., an external drive in wired or wireless communication with the controlling unit 900) or may be provided by a transitory or non-transitory computer-readable medium. Examples of non-transitory computer readable media include a RAM, a ROM, an EPROM, an EEPROM, a flash memory, a CDROM, or other portable memory storage.

The controlling unit 900 may also include one or more storage units 910, such as a mass storage unit. The controlling unit 900 may include one or more network interfaces 912 for wired or wireless communication with a network (e.g., an intranet or the Internet).

The controlling unit 900 may include one or more input devices 914 (e.g., a keyboard or a mouse) and one or more output devices 916 (e.g., a display screen). There may be a bus 918 providing communication among the components of the controlling unit 900.

The controlling unit 900 may be able to carry out other processing suitable for generating a $T_1$ map, including providing user interfaces and image processing operations.

Example Studies

An example of the IG fitting technique was validated using simulations, phantom, and in vivo experiments. Three different MOLLI acquisition types were used. The first acquisition was a conventional 5(3)3 inversion grouping. The second two, 5(0)3 and 1(0)2(0)3(0)5, had no rest periods.

FIG. 2 shows plots of simulated MOLLI data together with $T_1$ fits. Two different inversion groupings were simulated: 5(3)3 and 1(0)2(0)3(0)5. $T_1$ fits were performed with a conventional 3-parameter model, as well as an example of the disclosed IG model. The "*" symbols correspond to the fitted model. All other symbols represent the simulated data. The data associated with each inversion grouping has a different symbol. For the 5(3)3 acquisition, there is almost complete recovery between inversion groupings. Therefore, all inversion groupings substantially follow the same recovery curve. In this case, the *'s and the other symbols substantially lie on top of each other. For the 1(0)2(0)3(0)5 acquisition, there is incomplete magnetization recovery between inversion groupings. Therefore, the inversion groupings do not follow the same recovery curve. The conventional 3-parameter model does not take this into account. Therefore, the *'s and the other symbols do not lie on top of each other. However, the example disclosed IG model does take this into account, and the * symbols lie substantially on top of the other symbols in this case.

Figure 4:
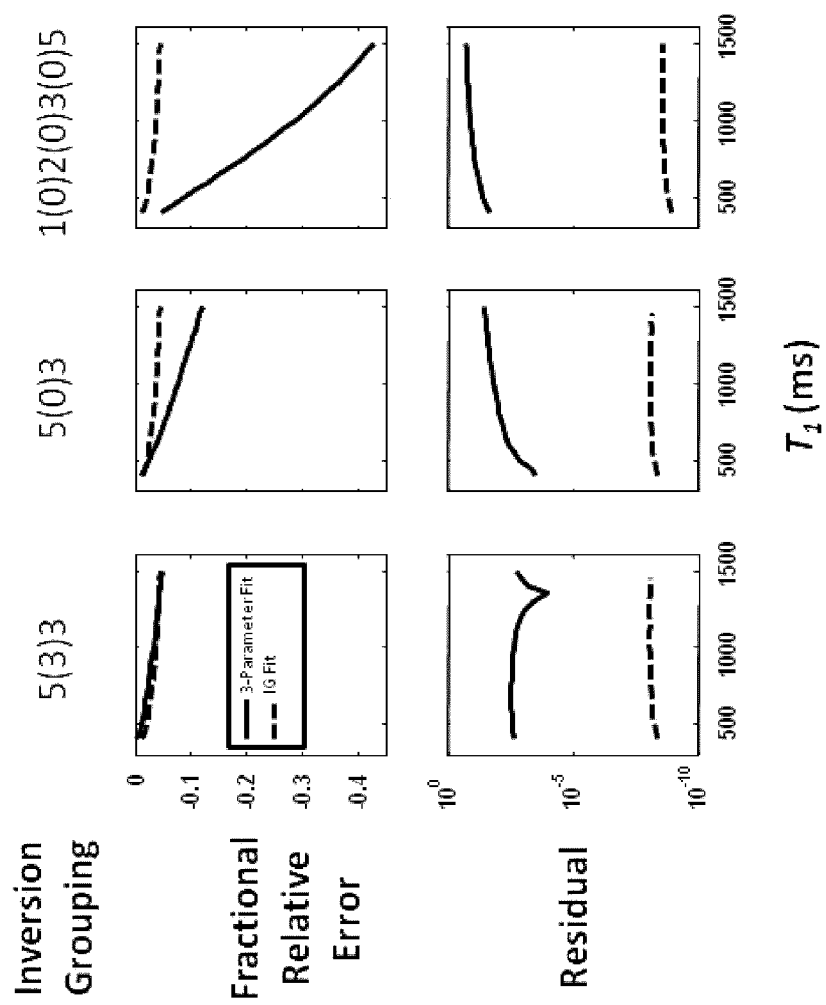
FIG. 4 shows plots of fractional relative error and residuals from simulations comparing the MOLLI technique with an example of the present disclosure.

Further simulation results are plotted in FIG. 4. The simulation was performed for three different inversion groupings: 5(3)3, 5(0)3, 1(0)2(0)3(0)5. In FIG. 4, the top half of the figure plots the fractional relative $T_1$ error for the conventional 3-parameter fit and an example of the disclosed IG fit technique. These plots illustrate the discrepancy between fitted and true $T_1$ values for the three inversion groupings. In the case of the 5(3)3 grouping, the 3-parameter and IG fits both yield acceptably small and similar errors. This is likely due to the almost complete magnetization recovery between inversion groupings. In the case of the other two groupings, the 3-parameter fitting technique produces unacceptably large errors. The discrepancy is more pronounced as $T_1$ gets longer, as there is less magnetization recovery between inversion groupings. On the other hand, the IG fitting technique provides consistent fits with acceptably small errors for all inversion groupings.

The bottom half of the figure plots the square root of the sum-of-square residuals of the fits. In all cases, the IG fit residuals are at least five orders of magnitude smaller than the 3-parameter fit residuals. Also note that in contrast to the 3-parameter fit, the IG fit residuals are roughly the same order of magnitude across all inversion groupings. This indicates a consistent quality of fit.

Figure 5:
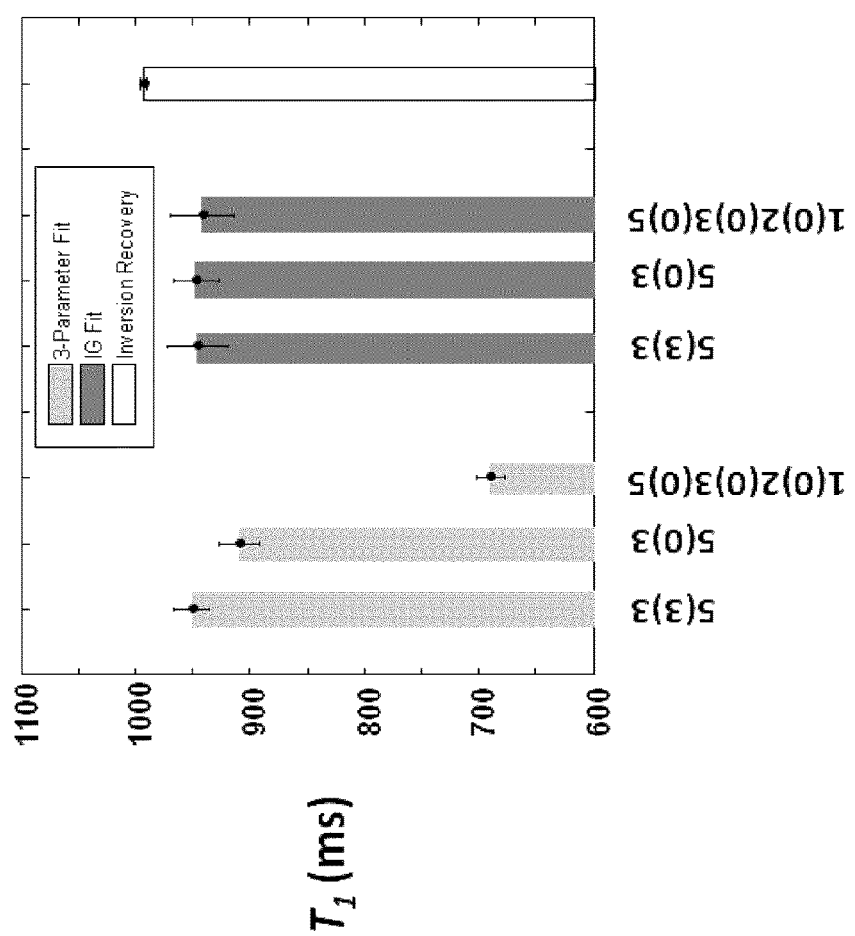
FIG. 5 is a plot showing experimental results comparing the MOLLI technique with an example of the present disclosure, using a phantom.

FIG. 5 is a plot from a MOLLI phantom experiment using a vial of $MnCl_2$-doped water. Images were acquired with three different inversion groupings. For each grouping, $T_1$ fitting was performed with both the conventional 3-parameter and example disclosed IG techniques. An inversion recovery sequence was also performed to provide the true $T_1$ value (=992+/−3 ms). The data is presented as the mean and standard deviation over an ROI in the vial. An offset from the true $T_1$ value is seen in this example plot, which is due to the bias inherent in MOLLI-type acquisitions, as discussed above. This bias may be corrected for using suitable techniques.

Qualitatively, the $T_1$ values associated with the 3-parameter fit show significant variation over the inversion groupings. In contrast, the $T_1$ values derived with the IG fit appear very consistent. Quantitatively, there is a significant statistical difference in $T_1$ values between every inversion grouping for the 3-parameter fit. There is no statistical difference between any of the inversion groupings in the case of the IG fit. In comparing the fits among the individual inversion groupings, there was no statistical difference between the $T_1$ values of the 3-parameter and IG fits for the 5(3)3 grouping (p=0.25). There was a significant difference in $T_1$ for the cases of the 5(0)3 and 1(0)2(0)3(0)5 groupings (p≈0 in both cases).

The $\chi^2$ values of all fits performed with the IG technique were acceptable within the limits of noise. For the 3-parameter fits, the 5(3) and 5(0)3 fits were acceptable, while the 1(0)2(0)3(0)5 fit was not (p≈0).

Figure 6:
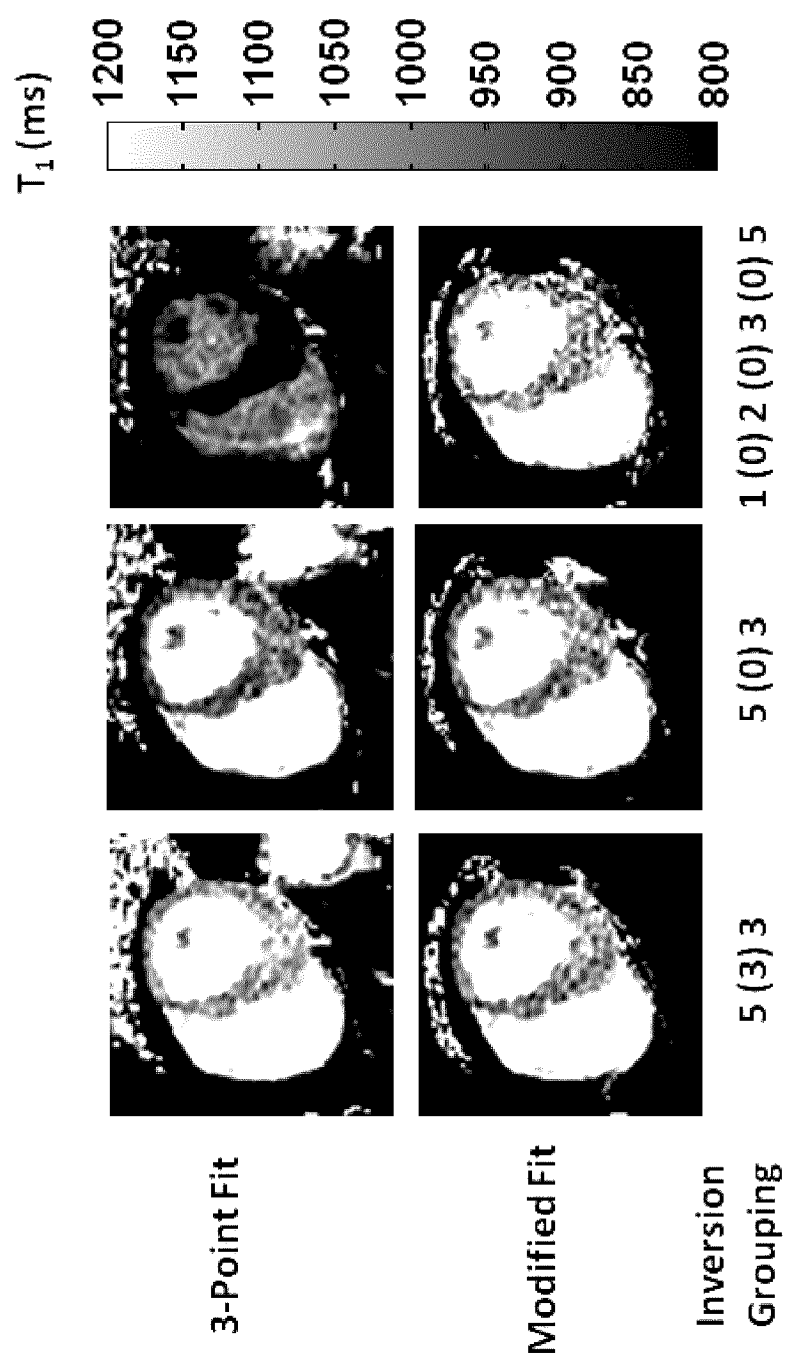
FIG. 6 shows example T1 maps generated in a human subject using the MOLLI technique compared to an example of the present disclosure.

FIG. 6 illustrates results from an in vivo example comparing the conventional 3-parameter (or 3-point) fitting technique to an example of the disclosed IG fitting technique. In FIG. 6, $T_1$ maps for different inversion groupings are windowed to highlight the myocardium. With the conventional 3-parameter fit, there are obvious changes in the fitted $T_1$ values across the different inversion groupings. In contrast, the IG fitting technique provides consistent $T_1$ values for all inversion groupings. Note that the colormap in this figure is set to highlight the $T_1$'s in the myocardium.

In various examples, the present disclosure provides methods and systems for performing $T_1$ fitting using two parameters, plus one parameter per inversion grouping. In contrast, conventional MOLLI fitting uses three parameters for all inversion groupings. Examples of the disclosed IG technique may provide robust $T_1$ results for any combination of inversion groupings and rest periods (including no rest period). For example, the present disclosure may permit acquisitions that have larger inversions groupings towards the end of the acquisition (also referred to as back-loaded acquisitions), rather than towards the beginning (also referred to as front-loaded acquisitions) as is conventionally done. This may differ from conventional fitting techniques where the fitted $T_1$ value may vary significantly with different inversion groupings.

In some examples, the present disclosure may permit shorter scan times than conventional MOLLI fittings, since rest periods may be eliminated. This may make the technique less sensitive to respiratory motion and arrhythmias. In some examples, the present disclosure may allow a better optimization of $T_1$ accuracy and precision, since the disclosed IG technique potentially allows more TI acquisitions in the same total scan time period (e.g., by eliminating or reducing the rest period). In some examples, the disclosed IG technique may be less sensitive to different heart rates than conventional fitting techniques. This is due to the fact that the IG technique may not require complete magnetization recovery between inversion groupings. In contrast, the conventional method does. Other possible advantages of the disclosed technique over conventional techniques may include, for example, the ability to address incomplete magnetization recovery in case of an arrhythmia, as well as the ability to perform a free-breathing navigator scan without overly prolonging the time required for the scan.

Although the present disclosure describes examples for $T_1$ mapping for cardiac imaging, the present disclosure may be applied (with suitable modifications, as appropriate) to other fitting scenarios (besides $T_1$ mapping and MOLLI) that use groups of data separated by a rest period, as well as to other areas besides the heart. In some examples, the present disclosure may be beneficial in the context of motion-compensated scans.

The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entirety.

REFERENCES

1. Messroghli, D. R., et al., Modified Look-Locker inversion recovery (MOLLI) for high-resolution T-1 mapping of the heart. Magnetic Resonance in Medicine, 2004. 52(1): p. 141-146.
2. Messroghli, D. R., et al., Optimization and validation of a fully-integrated pulse sequence for modified look-locker inversion-recovery (MOLLI) T1 mapping of the heart. Journal of Magnetic Resonance Imaging, 2007. 26(4): p. 1081-1086.
3. Piechnik, S. K., et al., Normal variation of magnetic resonance T1 relaxation times in the human population at 1.5 T using ShMOLLI. Journal of Cardiovascular Magnetic Resonance, 2013. 15.
4. Piechnik, S. K., et al., Shortened Modified Look-Locker Inversion recovery (ShMOLLI) for clinical myocardial T1-mapping at 1.5 and 3 T within a 9 heartbeat breathhold. Journal of Cardiovascular Magnetic Resonance, 2010. 12.
5. Deichmann, R. and A. Haase, *QUANTIFICATION OF T1 VALUES BY SNAPSHOT-FLASH NMR IMAGING*. Journal of Magnetic Resonance, 1992. 96(3): p. 608-612.
6. Kellman, P., D. A. Herzka, and M. S. Hansen, *Adiabatic Inversion Pulses for Myocardial T1 Mapping*. Magnetic Resonance in Medicine, 2014. 71(4): p. 1428-1434.
7. Hargreaves, B. A., et al., *Characterization and reduction of the transient response in steady-state MR imaging*. Magnetic Resonance in Medicine, 2001. 46(1): p. 149-158.
8. Jaynes, E. T., *MATRIX TREATMENT OF NUCLEAR INDUCTION*. Physical Review, 1955. 98(4): p. 1099-1105.

The invention claimed is:

1. A method for determining T1 value, comprising:
obtaining T1 samples from an acquisition that includes one or more inversion groupings;
applying a model in which fit parameters are variable dependent on each inversion grouping; and
determining a calculated T1 value using the fit parameters calculated using the model;
wherein the calculated T1 value corresponds to a pixel of an image and the calculated T1 value is used for generating a T1 map for the image.

2. The method of claim 1, wherein the acquisition includes variable preparatory pulses.

3. The method of claim 1, further comprising calculating a combined T1 value using calculated T1 values from different inversion groupings.

4. The method of claim 1, further comprising performing the acquisition and obtaining the T1 samples from the performed acquisition.

5. The method of claim 1, wherein the acquisition is designed to result in incomplete tissue magnetization recovery between at least two inversion groupings.

6. The method of claim 5, wherein there is no rest period between at least two inversion groupings.

7. The method of claim 1, wherein the T1 samples are retrieved from a historical database.

8. The method of claim 1, wherein the T1 value is determined for cardiac tissue.

9. The method of claim 1, further comprising generating the T1 map by calculating the calculated T1 value over the image.

10. The method of claim 1, wherein the model has the equation $$S_i(A, B_1, \ldots, B_i, T_1^*; TI) \equiv A - B_i e^{-\frac{TI}{T_1^*}}; i = 1, \ldots, n;$$

where $S_i$ is the signal behavior of inversion group i, $T_1^*$ is the observed $T_1$ value, A is the steady state magnetization, and $B_i$ is defined as:

$$B_i = (M0_i + M0_i^*);$$

where $M0_i$ is the magnitude of magnetization immediately prior to each inversion pulse, and $M0_i^*$ is the steady state magnetization for each inversion grouping.

11. The method of claim 10, wherein the calculated T1 value is determined using the equation $$T_{1_i} = T_1^* \cdot \left(\frac{B_i}{A} - 1\right) \Big/ \delta_i;$$

where $\delta_i$ is the fraction of magnetization prior to the $i^{th}$ inversion pulse.

12. The method of claim 1, wherein inversion fractions are determined based on a simulation of the magnetization.

13. The method of claim 12, wherein the T1 value is determined from the equation: $T_1 = \sqrt{\Sigma_{i=1}^{n} T_{1_i}^{*2}}$.

14. The method of claim 1, wherein inversion fractions are determined using the equation $$\delta_{i_r} = \frac{T_{1_r}^*}{T_{1_1}^*}.$$

15. The method of claim 1, further comprising determining a plurality of calculated T1 values corresponding to respective pixels of the image and generating the T1 map for the image using the plurality of calculated T1 values.

16. A system for determining T1 value, comprising a processing device for executing computer-executable instructions that, when executed, cause the system to:
obtain T1 samples from an acquisition that includes one or more inversion groupings;
apply a model in which fit parameters are variable dependent on each inversion grouping; and
determine a calculated T1 value using the fit parameters calculated using the model;
wherein the calculated T1 value corresponds to a pixel of an image and the calculated T1 value is used for generating a T1 map for the image.

17. The system of claim 16, wherein the acquisition includes variable preparatory pulses.

18. The system of claim 16, wherein the instructions further cause the system to calculate a combined T1 value using calculated T1 values from different inversion groupings.

19. The system of claim 16, wherein the acquisition is designed to result in incomplete tissue magnetization recovery between at least two inversion groupings.

20. A non-transitory computer readable medium having instructions tangibly encoded thereon, wherein the instructions, when executed by a processing device, causes the processing device to:
  obtain T1 samples from an acquisition that includes one or more inversion groupings;
  apply a model in which fit parameters are variable dependent on each inversion grouping; and
  determine a calculated T1 value using the fit parameters calculated using the model;
  wherein the calculated T1 value corresponds to a pixel of an image and the calculated T1 value is used for generating a T1 map for the image.

* * * * *